(12) United States Patent
Pham

(10) Patent No.: US 10,357,651 B2
(45) Date of Patent: Jul. 23, 2019

(54) METHOD OF MANUFACTURING A FLEXIBLE CONDUCTIVE TRACK ARRANGEMENT, FLEXIBLE CONDUCTIVE TRACK ARRANGEMENT AND NEUROSTIMULATION SYSTEM

(71) Applicant: KONINKLIJKE PHILIPS N.V., Eindhoven (NL)

(72) Inventor: Hoa Pham, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 120 days.

(21) Appl. No.: 15/311,663

(22) PCT Filed: May 18, 2015

(86) PCT No.: PCT/EP2015/060869
§ 371 (c)(1),
(2) Date: Nov. 16, 2016

(87) PCT Pub. No.: WO2015/180988
PCT Pub. Date: Dec. 3, 2015

(65) Prior Publication Data
US 2017/0080216 A1    Mar. 23, 2017

(30) Foreign Application Priority Data

May 28, 2014   (EP) .................................... 14170341

(51) Int. Cl.
 *A61N 1/05* (2006.01)
 *A61B 5/04* (2006.01)
 *A61B 5/0478* (2006.01)

(52) U.S. Cl.
CPC ........ *A61N 1/0551* (2013.01); *A61B 5/04001* (2013.01); *A61B 5/0478* (2013.01);
(Continued)

(58) Field of Classification Search
CPC .. A61N 1/0551; A61N 1/0541; A61N 1/0534; A61B 5/04001; A61B 5/0478; A61B 2562/125

See application file for complete search history.

(56) References Cited

U.S. PATENT DOCUMENTS 7,706,887 B2 *  4/2010  Tai ........................ B81C 1/0023
                                                      257/678
8,781,600 B2    7/2014  Janik
(Continued)

FOREIGN PATENT DOCUMENTS

EP           2626110 A1     8/2013
WO    WO2010055442 A1       5/2010
WO    WO2013156527 A1      10/2013

OTHER PUBLICATIONS

Rousche P.J. et al., "Flexible Polyimide-Based Intracortical Electrode Arrays with Bioactive Capability", IEEE Transactions on Bio-Medical Engineering, vol. 48, No. 3, p. 361-371, Mar. 2001.
(Continued)

*Primary Examiner* — Mark Bockelman
(74) *Attorney, Agent, or Firm* — Larry Liberchuk

(57) ABSTRACT

Disclosed is a method of manufacturing a flexible conductive track arrangement for a neurostimulation system such as a cochlear implant device. The method allows for the arrangement to be manufactured without the need for a transfer substrate by embedding the metal structures of the arrangement in a ceramic dielectric material formed in an atomic layer deposition process, which can be performed at a temperature that is compatible with the polymer processing steps of such an arrangement. A flexible conductive track arrangement and a neurostimulation system are also disclosed.

5 Claims, 5 Drawing Sheets

(52) U.S. Cl.
CPC ......... *A61N 1/0534* (2013.01); *A61N 1/0541* (2013.01); *A61B 2562/125* (2013.01)

(56) References Cited

U.S. PATENT DOCUMENTS

| | | |
|---|---|---|
| 9,387,318 B2 | 7/2016 | Martens |
| 2006/0251875 A1 | 11/2006 | Carlisle |
| 2012/0310258 A1 | 12/2012 | Llinas |
| 2013/0204318 A1 | 8/2013 | Young |
| 2013/0296658 A1 | 11/2013 | Souriau |
| 2013/0345780 A1 | 12/2013 | Tabada |
| 2017/0274199 A1* | 9/2017 | Decker ................ A61N 1/0484 |

OTHER PUBLICATIONS

Zhang Y. et al., "Electroplating to Visualize Defects in Al2O3 Thin Films Grown Using Atomic Layer Deposition", Thin Solid Films, vol. 517, (2009), pp. 3269-3272.

* cited by examiner

METHOD OF MANUFACTURING A FLEXIBLE CONDUCTIVE TRACK ARRANGEMENT, FLEXIBLE CONDUCTIVE TRACK ARRANGEMENT AND NEUROSTIMULATION SYSTEM

FIELD OF THE INVENTION

The present invention relates to a method of manufacturing a flexible conductive track arrangement comprising a distal portion comprising a plurality of electrodes, a proximal portion comprising a plurality of contacts and a strip in between the distal portion and the proximal portion, said strip comprising a plurality of conductive tracks each connecting an electrode to a contact.

The present invention further relates to such a flexible conductive track arrangement.

The present invention yet further relates to a neurostimulation system including such a flexible conductive track arrangement.

BACKGROUND OF THE INVENTION

Medical implantable devices for neurostimulation and/or detection are becoming increasingly commonplace as manufacturing processes allow for such devices to be produced with small enough form factors to facilitate implantation. Such devices may for instance comprise conductive tracks wound tightly around a carrier, e.g. a lead body or the like. The conductive tracks are for example required to relay signals between a sensor or electrode arrangement within the body and processing circuitry outside the body. The implantable part of the device needs to have certain dimensions, which for instance may depend on the particular implementation. One specific example is for deep brain stimulation, and another example is for cochlear implants.

For example, the cochlea of the human ear contains hair cells that are essential to the perception of sound. Sound vibrations distort certain structures of the cochlea which in turn distort the hair cells. This initiates electrical impulses in the hair cells which are conveyed to the fibers of the auditory nerve and ultimately to the brain.

Some instances of human hearing loss are attributed to extensive destruction of the hair cells. When this occurs, though the structures of the cochlea may otherwise be substantially intact, and the auditory nerve may be partially or completely intact, the auditory response is significantly impaired or non-existent.

Cochlear implants directly stimulate the auditory nerves inside the inner ear. In a traditional cochlear implant system, a microphone acquires sound from the environment. The sound is then selectively filtered by a speech processor, using various filter bank strategies such as Fast Fourier Transforms, to divide the signal into different frequency bands. Once processed, the signal is then sent to a transmitter, a coil held in position by a magnet placed behind the external ear. This transmitter sends the processed signal to the internal device by electromagnetic induction.

Embedded in the skull, behind the ear is a receiver which converts the signal into electric impulses and sends them through an internal cable to electrodes. Conventional cochlear implants are made of multiple platinum electrodes or similar conductive material, connected to platinum wire and embedded in a silicone body. These electrodes then act to stimulate the auditory nerve fibers by generating an electric field when the electrical current is routed to them.

The implant should have a small insertion area so that the installation of the cochlear implant does not damage the fine cochlear structures in the ear. Implants for deep brain stimulation or other nerve stimulation may or have similar constraints on the cable dimensions and insertion area. One known design is based on a long strip of electrodes, which are then wound around a carrier to form a spiral strip cochlear implant. This provides the desired tubular shape for insertion into the cochlea. An example of this type of arrangement is disclosed in US 2012/0310258.

A typical viable manufacturing process of such a strip is shown in FIG. 1. The process commences in step (a) with the provision of a silicon substrate 10 onto which a ceramic dielectric layer or layer stack 12 is deposited using plasma-enhanced chemical vapour deposition (PECVD). Such a ceramic dielectric layer typically comprises $SiO_x$ (x>1) and optionally further comprises a silicon nitride layer ($Si_3N_4$). In step (c) metal electrodes 14 are formed on the ceramic dielectric layer (stack) 12, e.g. through deposition and patterning of one or more metal layers.

A further ceramic dielectric layer (stack) 16 is deposited using PECVD in step (d), which may be made of the same dielectric material(s) as the ceramic dielectric layer (stack) 12, such that the electrodes 14 are encapsulated by the ceramic dielectric layer (stack) 12 and the further ceramic dielectric layer (stack) 16, after which in step (e) a biocompatible electrically insulating polymer layer 18 such as a parylene layer is coated onto the further ceramic dielectric layer (stack) 16, e.g. through spin-coating or dip-coating. Next, a glass transfer substrate 20 is glued to the biocompatible electrically insulating polymer layer 18 using adhesive 22 in step (f), followed by the removal of the silicon substrate 10, e.g. through etching or by the removal of a sacrificial release layer (not shown) in between the silicon substrate 10 and the ceramic dielectric layer (stack) 12 in step (g). At this stage, the ceramic dielectric layer or layer stack 12 may be patterned to form trenches 13 providing access to the electrodes 14.

In step (h), a further biocompatible electrically insulating polymer layer 24 such as another parylene layer is deposited, e.g. through spin-coating or dip-coating, on the ceramic dielectric layer (stack) 12 such that the strip is embedded in the biocompatible electrically insulating polymer layer 18 and the further biocompatible electrically insulating polymer layer 24. At this stage the further biocompatible electrically insulating polymer layer 24 may be patterned to form trenches 25 providing access to the electrodes 14 through trenches 13. The strip is finalized in step (i) by the removal of the glass transfer substrate 20, e.g. by dissolving the adhesive 22.

This process involves both ceramic and polymer processing steps, which typically require different temperature budgets. Specifically, the PECVD steps are typically performed at a temperature in excess of 120° C. using tetraethyl orthosilicate (TEOS) as a silicon oxide precursor, at which temperatures most biocompatible electrically insulating polymers such as parylene degrade or even decompose.

EP 2 626 110 A1 discloses a thin film for a lead for brain applications with at least one section comprising a high conductive metal and a low conductive metal, whereby the low conductive metal at least partially encapsulates the high conductive metal and is biocompatible.

SUMMARY OF THE INVENTION

Although the prior art process described above is practicable, it results in a flexible layer stack design that is relatively difficult to bend or wind to winding diameters sufficiently tight for the stack to be reliably used in e.g. a cochlear implant or other implants that require electrode inserts with small dimensions. This is especially so when the stack includes layers of inorganic and metallic nature.

The invention seeks to provide a flexible conductive track arrangement with a layer stack design that at least partly solves the tight winding drawback, while at the same time can be manufactured with improved practicability (e.g. simpler method and/or more cost effective). The invention accordingly also provides a method of manufacture for the flexible conductive track arrangement.

The invention is defined by the independent claims. The dependent claims provide advantageous embodiments.

The improved bending or winding properties of the flexible conductive track arrangement of the invention is based on the recognition that the bending or winding of the comparable prior art layer stack is improved by providing it with at least one substantially flat outer surface and a thinner layer stack. The flat surface enables a smoother winding around a central conductive track carrier or rod. This becomes increasingly important for smaller winding diameters. Furthermore, part of the thickness of the prior art layer stack design is due to the ceramic dielectric layer thickness which needs to be in the order of 500 nm in order to provide reliable electrical, and/or mechanical and/or material insulation for the embedded metal layer. Such thicknesses limit the flexibility of the strip, which may prohibit the use of the strip in application domains where a particularly tight winding of the strip around a carrier is required. The device of the invention now has the advantage that it can be made with one and the same method of manufacturing. Thus, both the flat surface and the thinner layer may be prepared with the same method. The method is also technically simpler and more practicable than the prior art method.

It is noted that with the method of the prior art it is not straight forward to prepare a thinner layer stack design. For one, reducing the layer thickness of the ceramic dielectric below approximately 500 nm in general leads to ceramic dielectric layers of insufficient quality, as thinner layers may suffer from degradation of the electrically insulating properties due to the defect density in such PECVD ceramic layers. This is particularly applicable when PECVD silicon oxide layers are formed from TEOS, as it is well-known per se that such oxide layers have a relatively high defect density.

In the invention, the dielectric layer stack may have a thickness or a maximum thickness of less than any number chosen from the group of: 500 nm, 400 nm, 300 nm, 250 nm, 200 nm, 150 nm, 100 nm and 50 nm. Preferably the thickness or maximum thickness is less than 300 nm or even more preferred is less than 200 nm. Such values yield a flexible conductive track arrangement in which bending stresses are reduced upon bending the arrangement. This therefore provides a flexible conductive track arrangement that can be wound tightly around a carrier such as a lead body for insertion into the human body, e.g. implantation in the cochlea or brain. In particular, by controlling the thickness of the dielectric layers and/or dielectric layer stack formed by the first and further dielectric layers or layer stacks, the stress in the overall dielectric layer stack can be controlled, e.g. tuned based on the expected curvature of the device.

The flexibility or bendability of the flexible conductive track arrangement is further improved in that the biocompatible polymer layer has a major surface that is substantially flat. With the method of the invention, one of the biocompatible polymer layers is formed directly on the substrate or the release layer on the substrate, whereas in the prior art method of FIG. 1 the biocompatible polymer layers are always formed over a stepped structure, thereby yielding a biocompatible polymer layer arrangement in which the major surfaces have stepped profiles. The substantially flat major surface of the biocompatible polymer layer of the flexible conductive track arrangement in accordance with the above embodiment facilitates a tighter winding of the flexible conductive track arrangement around the carrier such as a lead body such as e.g. central circular or oval rod.

A flexible conductive track arrangement can have a smaller insertion area, because of tighter winding of the conductive track arrangement enabled by the corrugations in it. Thus, one or more of the cross sectional dimension of the wound track (e.g. the diameter if it is of tubular shape) may be smaller than 1 mm or, as preferred for cochlea devices smaller than 0.5 mm or even 0.4 mm or 0.3 mm. The carrier can have a number of shapes according to desire. Example shapes include tubular or cylindrical with rectangular, oval or circular crosssection or even other crosssections. Preferably the crosssection is oval or circular. The carrier may have a smaller crosssection at one location than on another location. Hence it can be conical, or have sections of different but constant diameter wherein the smallest dimension can be smaller than 1 mm or even smaller than 0.5 mm. Alternatively, the carrier can be bar shaped with somewhat rounded edges extending in the bar extension direction.

The dielectric layer may comprise any suitable dielectric material, i.e. electrically insulating, material or combination of dielectric materials, e.g. multiple stacked layers of different dielectric materials. Such materials preferably are inorganic oxide material as these have good adhesion with the metals and provide good electrical, mechanical and material insulation properties. For instance, the dielectric layer stack may comprise layers individually or together comprising at least one of silicon oxide, silicon nitride and aluminium oxide. Other dielectric materials include high-k oxides such as zirconium oxide or hafnium oxide, and/or other nitrides having suitable barrier properties, e.g. titanium nitride or tantalum nitride may also be contemplated.

The dielectric layer of the conductive stack may be obtained or obtainable by atomic layer deposition. Such layers have very good insulation properties. Thus, the flexible conductive track arrangement may be manufactured by one or more embodiments of the method of the present invention. Such a flexible conductive track arrangement benefits from the intrinsically low defect density that is characteristic of ALD dielectric layers, which facilitates the provision of a flexible conductive track arrangement having improved properties compared to prior art arrangements as e.g. described above. Such layers can be thinner than those of the prior art method described above while they have similar or better electrical, material, mechanical insulating properties.

According to the invention there is also provided a neurostimulation and/or neurosensing device comprising the flexible conductive track arrangement according to at least one embodiment of the present invention and a neurostimulation/sensing unit having a plurality of further contacts for contacting respective contacts of the proximal portion of the flexible conductive track arrangement. Such a neurostimulation and/or sensor device benefits from the presence of a flexible conductive track arrangement according to an embodiment of the present invention due to the fact that such a flexible conductive track arrangement may have improved properties compared to prior art arrangements, such as improved flexibility as explained above.

The flexible conductive track and/or the neurostimulation and/or neurodetection device can be advantageously used for applications requiring small electrode inserts. Examples of such use are in cochlear devices including implantable cochlear devices.

According to the invention there is also provided a method of manufacture of a flexible conductive track arrangement.

The method allows fabrication of the inventive device as indicated above. Furthermore, the drawback of the known process is that it is a relatively complex process requiring a substrate transfer process in which the polymer processing steps are performed upon completion of the ceramic processing steps. Such process is necessary as it avoids the exposure of the deposited polymers to harmful temperatures.

The present method is makes use of the insight that the ceramic dielectric layers of the flexible conductive track arrangement may be deposited using atomic layer deposition (ALD) techniques, which has the advantage that the ceramic dielectric layers may be formed at temperatures that are compatible with the required polymer processing steps in the manufacturing process of the flexible conductive track arrangement, such that these polymer processing steps do not have to be performed upon completion of the formation of the ceramic dielectric layers encapsulating the metal structures of the flexible conductive track arrangement. Consequently, this obviates the need to use a transfer substrate, which therefore significantly simplifies the manufacturing method compared to the prior art method shown in FIG. 1. This replacement of deposition method together with adjustment and omission of some of the steps of the prior art method results in the method of the invention that is capable of providing the improved device and is simpler than the known method. At this point it is mentioned that the method can be used to prepare the conductive track arrangement of the invention having the flat outer surface when the substrate has a flat deposition surface, and or to deposit layers of the reduced thicknesses below 500 nm as indicated above, the method can also be used to prepare arrangements that still have non-flat outer surfaces when substrate deposition surfaces used with the method are non-flat while layer thicknesses are reduced.

The atomic layer deposition steps can be performed at lower temperatures in order to save already present vulnerable layers of a half fabricate device. For example, the atomic layer deposition steps may be performed below 120° C., at which temperatures polymer materials such as parylene or polyimide do not degrade or decompose.

The step of depositing at least one dielectric layer on the first biocompatible polymer layer by atomic layer deposition may comprise depositing a first dielectric layer on the first biocompatible polymer layer and depositing a second dielectric layer on the first dielectric layer; and/or the step of depositing at least one further dielectric layer on the patterned metal layer by atomic layer deposition comprises depositing a first further dielectric layer on the patterned metal layer and depositing a second further dielectric layer on the first further dielectric layer. One of the advantages of atomic layer deposition is that relatively thin dielectric layers having low defect density may be formed, which facilitates the formation of dielectric layer stacks that have limited thickness but high integrity due to the low defect density that is characteristic of ALD processes.

Thicknesses as described for the arrangement above can be deposited using ALD. In a particularly advantageous embodiment, the at least one dielectric layer and the at least one further dielectric layer each are deposited to a thickness of less than 100 nm. This allows for the formation of a particularly flexible conductive track arrangement, as a dielectric layer stack in which the metal structures are embedded may be achieved having an overall maximum thickness of less than 200 nm, e.g. less than 100 nm, e.g. around 50 nm, without such a relatively thin dielectric layer stack compromising the electrical insulation and barrier properties of the dielectric layer stack due to the intrinsically low defect density in ALD dielectric layers.

The chemical composition of the dielectric layer material(s) deposited by means of the ALD process is not particularly limited; any suitable dielectric material, i.e. electrically insulating material, may be considered. In an embodiment, the at least one dielectric layer and/or the at least one further dielectric layer is individually selected from at least one of silicon oxide, silicon nitride or aluminium oxide although alternative dielectric materials, e.g. high-k oxides such as zirconium oxide or hafnium oxide, and/or other nitrides having suitable barrier properties, e.g. titanium nitride or tantalum nitride may also be contemplated.

The first biocompatible polymer layer and the second biocompatible polymer layer may each consist of an electrically insulating polymer. Any suitable biocompatible polymer that is electrically insulating may be used; for instance, the electrically insulating polymer may be selected from parylene and polyimide.

In an embodiment, the method further comprises providing a release layer on the substrate prior to the formation of the first biocompatible polymer layer, and wherein the step of removing said substrate comprises dissolving said release layer. This has the advantage that the substrate may be removed in a manner that minimizes the risk of damage to the flexible conductive track arrangement, e.g. by obviating the need for mechanical polishing steps or etching steps to disintegrate the substrate, which steps may damage the flexible conductive track if not terminated in time. The use of the release layer furthermore has the advantage that the substrate may be reused, thereby reducing the material budget of the manufacturing method, which may reduce the overall cost of the manufacturing process.

In the track and method of the invention, the substrate may be a polymeric substrate or an inorganic substrate. Preferably a wafer type or glass type substrate is used. In particular a silicon comprising wafer such as SOI or normal silicon wafer is used.

BRIEF DESCRIPTION OF THE DRAWINGS

Embodiments of the invention are described in more detail and by way of non-limiting examples with reference to the accompanying schematic drawings, wherein.

DETAILED DESCRIPTION OF THE EMBODIMENTS

Figure 1:
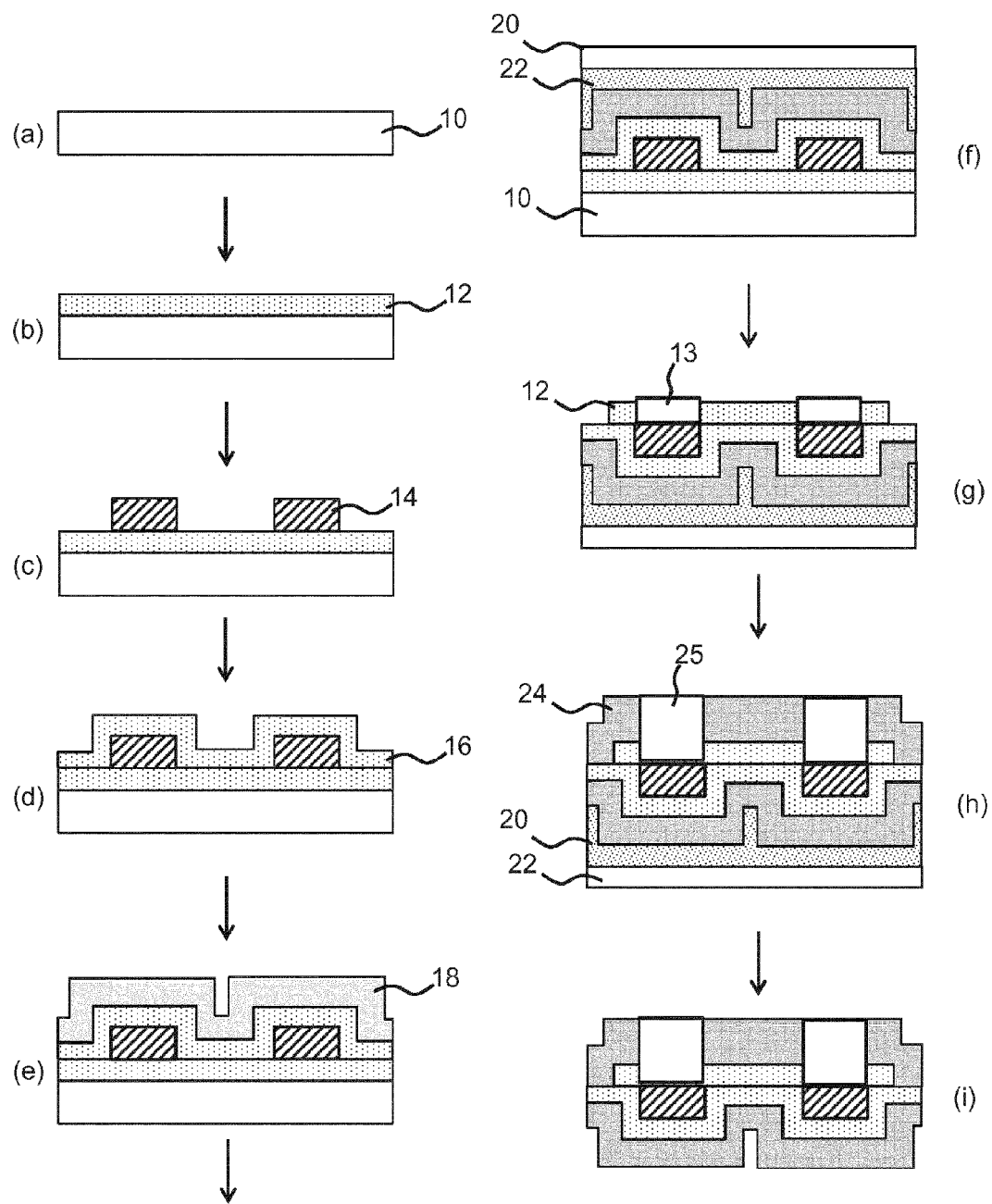
FIG. 1 schematically depicts a prior art manufacturing method of a flexible conductive track arrangement for an implantable device.

In the Figures, the same reference numerals are used to indicate the same or similar parts.

Figure 2:
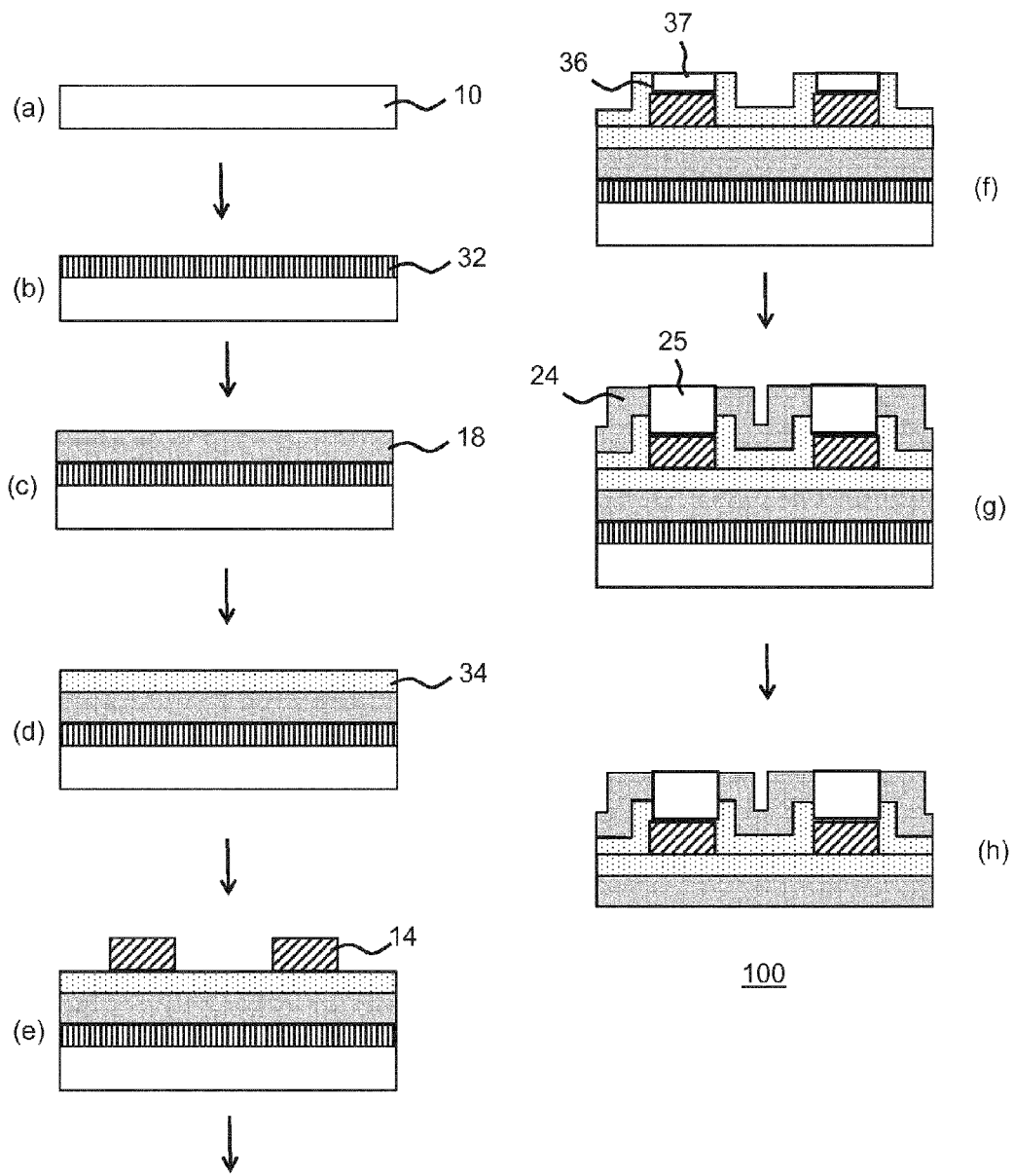
FIG. 2 schematically depicts a manufacturing method of a flexible conductive track arrangement for an implantable device according to an embodiment of the present invention.

FIG. 2 schematically depicts a manufacturing method of a flexible conductive track arrangement according to an example embodiment of the present invention. The method begins in step (a) with the provision of a substrate 10 on which the flexible conductive track arrangement is to be formed. Any suitable substrate 10 may be used for this purpose; for instance, if the flexible conductive track arrangement is to be formed using semiconductor processing steps the substrate 10 may be a silicon wafer. However, it should be understood that other substrates, e.g. glass substrates, may also be contemplated.

In an optional step (b), a release layer 32 may be formed on the substrate 10. Such a release layer 32 typically is a layer that can be removed by dissolving the release layer 32 in a suitable solvent, as will be explained in more detail later. In an embodiment, the release layer 32 is a photoresist layer, as such layers are well-known and are typically removed using suitable solvents. The release layer 32 may be formed to any suitable thickness, such as a thickness ranging from 2-3 micron. The method subsequently proceeds to step (c) in which a first biocompatible polymer layer 18 is formed on the substrate 10 or on the release layer 32. The first biocompatible polymer layer 18 may be formed in any suitable manner, such as by spin coating or dip coating or by chemical vapour deposition, and to any suitable thickness. Preferably, the thickness of the first biocompatible polymer layer 18 is chosen such that the overall thickness of the outer polymer shell of the flexible conductive track arrangement does not prohibit the desired bending or winding characteristics of the arrangement. In an embodiment, the thickness of the first biocompatible polymer layer is chosen in the range of 2-5 micron.

Any suitable biocompatible polymer may be selected, which polymer preferably is an electrically insulating polymer such that part of the body in which the flexible conductive track arrangement is implanted is shielded from the electric currents running through the flexible conductive track arrangement during use. For example, the biocompatible polymer may be parylene or polyimide.

Next, one or more dielectric layers 34 are formed on the first biocompatible polymer layer 18 by means of atomic layer deposition in step (d). Such dielectric layers protect the metal structures in the flexible conductive track arrangement from exposure to potentially harmful constituents in the environment of the flexible conductive track arrangement, such as corrosive constituents in bodily fluids. The dielectric layers act as barrier layers for such constituents. The ALD step typically is performed at a temperature below 120° C. such that the underlying first biocompatible polymer layer 18 is not degraded or decomposed by the temperature budget of the ALD step. In an embodiment, the ALD step is performed at a temperature below 100° C.

ALD can produce highly conformal layers having an extremely low defect density. Defect densities of less than 100/cm$^2$ and even less than 50/cm$^2$ have been reported for thin ALD dielectric layers; for instance, Y. Zhang et al. in Thin Solid Films, 517 (2009), pages 3269-3272 disclose a defect density of as little as 38/cm$^2$ for a 25 nm thick ALD Al$_2$O$_3$ layer. Consequently, the ALD dielectric layer or layer stack 34 of the invention may be grown to a thickness of less than 100 nm, e.g. a thickness of 50 nm, 40 nm, 30 nm, or even 20 nm without compromising the required properties of the ALD dielectric layer or layer stack 34. If a dielectric layer stack 34 is formed in step (d), the individual layers of this layer stack may be formed to an even smaller thickness such that the combined thickness of the dielectric layer stack 34 is less than 100 nm, e.g. has a thickness of 50 nm, 40 nm, 30 nm, or even 20 nm. This greatly enhances the flexibility of the flexible conductive track arrangement.

Any suitable dielectric material may be used for the formation of the ALD dielectric layer or layer stack 34. For instance, a silicon oxide layer may be deposited, a stack of a silicon oxide and silicon nitride layer may be deposited and so on. The use of alternative oxide and nitrides such as Al$_2$O$_3$, HfO$_2$, ZrO$_2$, TiN, TaN and so on may also be contemplated. Other suitable oxides and nitrides will be apparent to the skilled person. Any suitable layer combination of such oxides and nitrides, e.g. a layer stack comprising a nitride layer on the first biocompatible polymer layer 18 and an oxide layer on the nitride layer or a layer stack comprising an oxide layer on the first biocompatible polymer layer 18 and a nitride layer on the oxide layer may be contemplated.

Next, the metal structures 14 are formed on the first dielectric layer or layer stack 34 in step (e), e.g. by depositing and patterning one or more metal layers. The formation of such metal structures is well-known per se and will not be explained in further detail for the sake of brevity. The metals of which the metal structures are made preferably are biocompatible metals such as titanium. At least some of the electrodes, conductive tracks and/or contacts of the flexible conductive track arrangement may be formed as a bimetal, e.g. having a first metal core and a second metal cladding. The first metal may have a high conductivity, e.g. higher than the second metal, whereas the second metal may be cheaper than the first metal and/or may be biocompatible. For instance, the first metal may be a noble metal such as gold and the second metal may be a metal such as titanium.

The formation of such bimetallic structures is particularly suitable for the formation of the conductive tracks in the flexible conductive track arrangement as the high conductive core ensures that the overall thickness of the conductive tracks may be limited, thereby improving the flexibility of the flexible conductive track arrangement. In an embodiment, the thickness of the conductive tracks is in the range of 4-13 micron. The thickness of the conductive tracks is typically chosen based on the chosen thicknesses of the biocompatible polymer, electrodes and/or contacts and dielectric layers in the device. Any suitable thickness, e.g. thicknesses outside the range disclosed above, may be contemplated.

After the formation of the metal structures 14 in step (e), the method proceeds to step (f) in which a further dielectric layer or layer stack 36 is formed over the resulting structure using ALD, such that the metal structures 14 are embedded in a dielectric layer stack formed by the first dielectric layer or layer stack 34 and the further dielectric layer or layer stack 36. The further dielectric layer or layer stack 36 may be formed to the same thickness using the same materials as the first dielectric layer or layer stack 34, which has already been described above and will therefore not be described again for the sake of brevity only. However, it should be understood that the further dielectric layer or layer stack 36 may comprise different materials to the first dielectric layer or layer stack 34 and/or may be formed to a different thickness than the first dielectric layer or layer stack 34. The further dielectric layer or layer stack 36 is typically patterned, e.g. using suitable etch recipes, to form trenches 37 in the further dielectric layer or layer stack 36 that expose the electrodes and contacts in the proximal and distal portions of the device.

In step (g), a further layer 24 of the biocompatible polymer is formed over the further dielectric layer or layer stack 36, e.g. by spin coating, dip coating or by chemical vapour deposition, such that the dielectric layer stack formed by the first dielectric layer or layer stack 34 and the further dielectric layer or layer stack 36 is encapsulated by a biocompatible polymer layer formed by the first biocompatible polymer layer 18 and the further biocompatible polymer layer 24. The further layer 24 may be formed using the same polymer and/or to the same thickness as the first layer 18, which already has been described above and will therefore not be described again for the sake of brevity only. The further layer 24 is typically patterned, e.g. using a suitable etch recipe or solvent, to form trenches 25 in the further layer 24 that expose the electrodes and contacts in the proximal and distal portions of the device through the trenches 37.

In final step (h), the substrate 10 is removed to yield the flexible conductive track arrangement 100. The substrate 10 may be removed in any suitable manner, e.g. by etching, polishing or grinding, or in case of the presence of release layer 32, by dissolving the release layer 32 in a suitable solvent that does not dissolve or degrade the biocompatible polymer layers 18 and 24.

At this point, it is noted that because the first biocompatible polymer layer 18 is formed on the (planar) substrate 10 or on the (planar) release layer 32, the first biocompatible polymer layer 18, upon removal of the substrate 10 a flexible conductive track arrangement 100 is obtained that has a polymer shell having a substantially flat or planar major surface at the outside of the device, i.e. the surface of the first biocompatible polymer layer 18. This is advantageous because such a flat or planar surface facilitates a tight winding of the flexible conductive track arrangement 100 around a carrier such as a lead body or central rod, as will be explained in more detail later.

Figure 3:
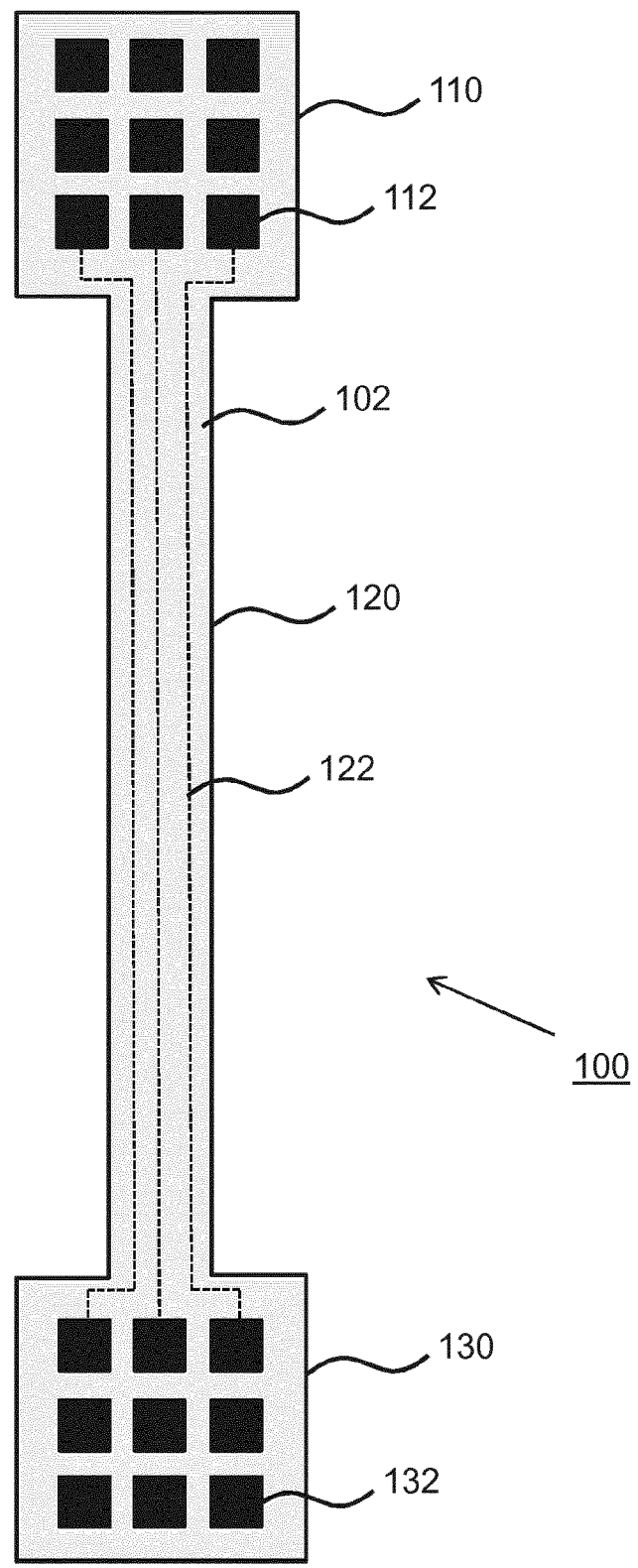
FIG. 3 schematically depicts a top view of a flexible conductive track arrangement for an implantable device according to an embodiment of the present invention.

FIG. 3 schematically depicts a top view of a flexible conductive track arrangement 100 according to an example embodiment of the present invention. The flexible conductive track arrangement 100 comprises a distal portion 110 including one or more electrodes 112 for contacting an area to be stimulated in a subject such as a human or animal subject. The area to be stimulated for instance may be in the cochlea or in the brain. The flexible conductive track arrangement 100 further comprises a proximal portion 130 including one or more contacts 132 that are connected to respective electrodes 112 through the conductive tracks 122 in the strip 120 interconnecting the proximal portion 130 to the distal portion 110. The strip 120 is typically wound around a carrier such as a lead body as will be explained in more detail below. The strip 120 may have any suitable dimensions; in particular the strip 120 may have a length of several tens of cm, e.g. 10 cm, 20 cm, 30 cm or even 50 cm and beyond.

The contacts 132 facilitate a signal source such as a neurostimulation and or detection device to control the one or more electrodes 112, e.g. by being connected to the one or more contacts 132 and providing electrical signals to the one or more electrodes 112 through the one or more contacts 132. For example, in case of the flexible conductive track arrangement 100 being a cochlear implant device, the neurostimulation device may include a microphone for collecting ambient sounds, a filter for filtering the ambient sounds, and a signal generator coupled between the filter and the contacts 132 for converting the filtered ambient sounds into stimuli that can be applied to the cochlea through the one or more electrodes 112.

Alternatively, the neurostimulation and/or neurodetection device may include a neurostimulation unit that includes a signal generator for generating predefined signals to be applied to a region of the brain for countering symptoms of neurological diseases such as Parkinson's disease, in which case the distal portion 110 of the flexible conductive track arrangement 100 is typically connected to an appropriate region of the brain via one or more of the electrodes 112.

Figure 4:
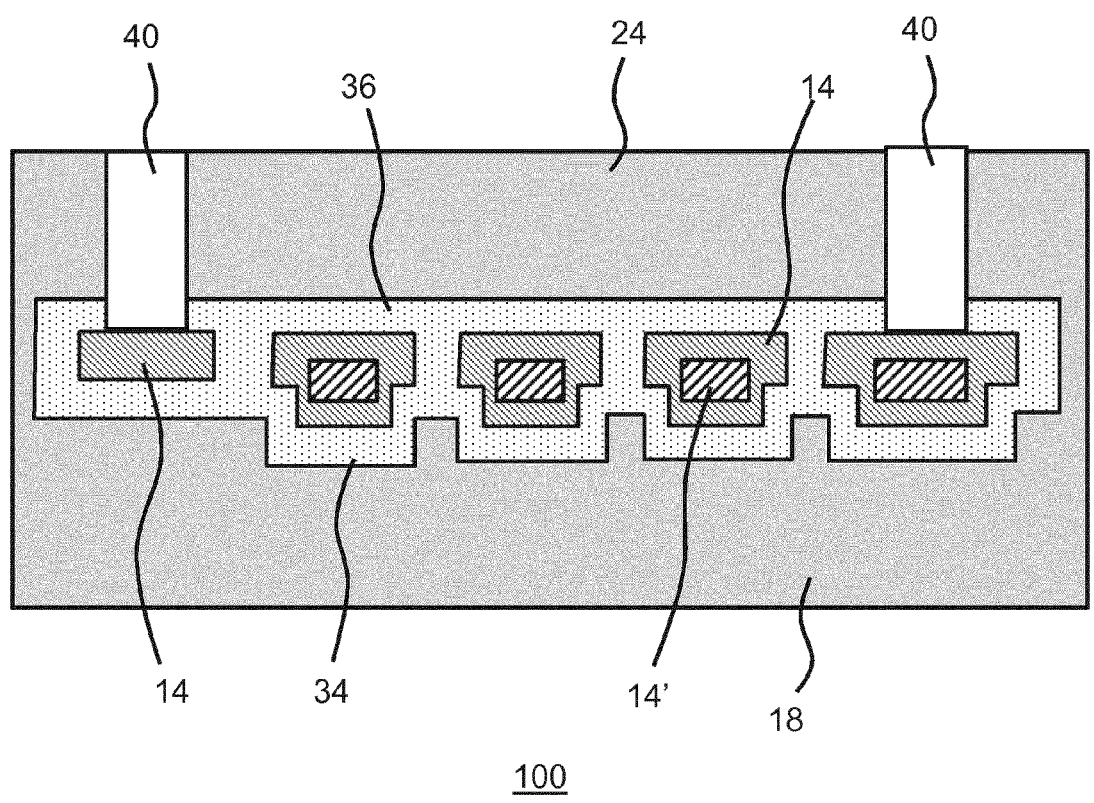
FIG. 4 schematically depicts a cross-section of a flexible conductive track arrangement for an implantable device according to an embodiment of the present invention.

FIG. 4 schematically depicts a cross-section in a length direction of a flexible conductive track arrangement 100 in accordance with an embodiment of the present invention and manufactured with the method of the invention. A number of metal structures, e.g. electrodes formed by a single metal structure 14, e.g. a titanium electrode, and/or electrodes formed by a bimetallic metal structure having a metal core 14', e.g. a gold core and a metal shell 14, e.g. a titanium shell, may be present. The metal structures are embedded in an ALD ceramic dielectric layer stack formed by the first dielectric layer or layer stack 34 and the further dielectric layer or layer stack 36, which ALD ceramic dielectric layer stack is characterised by a low defect density, which typically is several orders lower than the defect density of a PECVD dielectric layer stack of the same thickness. In at least some embodiments, the ALD ceramic dielectric layer stack has a maximum thickness of less than 200 nm, such as a maximum thickness of about 100 nm, or less then about 100 nm, e.g. about 50 nm. The ALD ceramic dielectric layer stack is embedded in a polymer coating formed by the first biocompatible polymer layer 18 and the further biocompatible polymer layer 24. It is reiterated that the first biocompatible polymer layer 18 typically has a substantially flat or planar surface, which facilitates a tight winding of the flexible conductive track arrangement 100 around a carrier, as the substantially flat or planar surface of the first biocompatible polymer layer 18 in combination with the relatively thin ALD ceramic dielectric layer stack ensures better control over the stress, i.e. a stress reduction, in the flexible conductive track arrangement 100 upon bending. At least one of the outer surfaces of the biocompatible layer 18 is substantially flat, therewith facilitating winding of the entire stack 100 around a central rod. The flat surface is due to the use of the method of the invention.

Access to electrodes 112 to be brought in contact with an area to be stimulated and access to contacts 132 may be provided by forming trenches or vias 40 in the flexible conductive track arrangement 100. As the formation of such trenches or via as is well-known per se, this is not explained in further detail for the sake of brevity only. Alternatively, several electrodes 112 and/or contacts 132 may be exposed by removing the polymer coating and the ceramic dielectric layer stack from selected areas of the distal portion 110 and/or the proximal portion 130. At this point, it is noted that the distal portion 110 and the proximal portion 130 are shown to have a square shape by way of non-limiting example only; it should be understood that the distal portion 110 and the proximal portion 130 may have any suitable shape.

Figure 5:
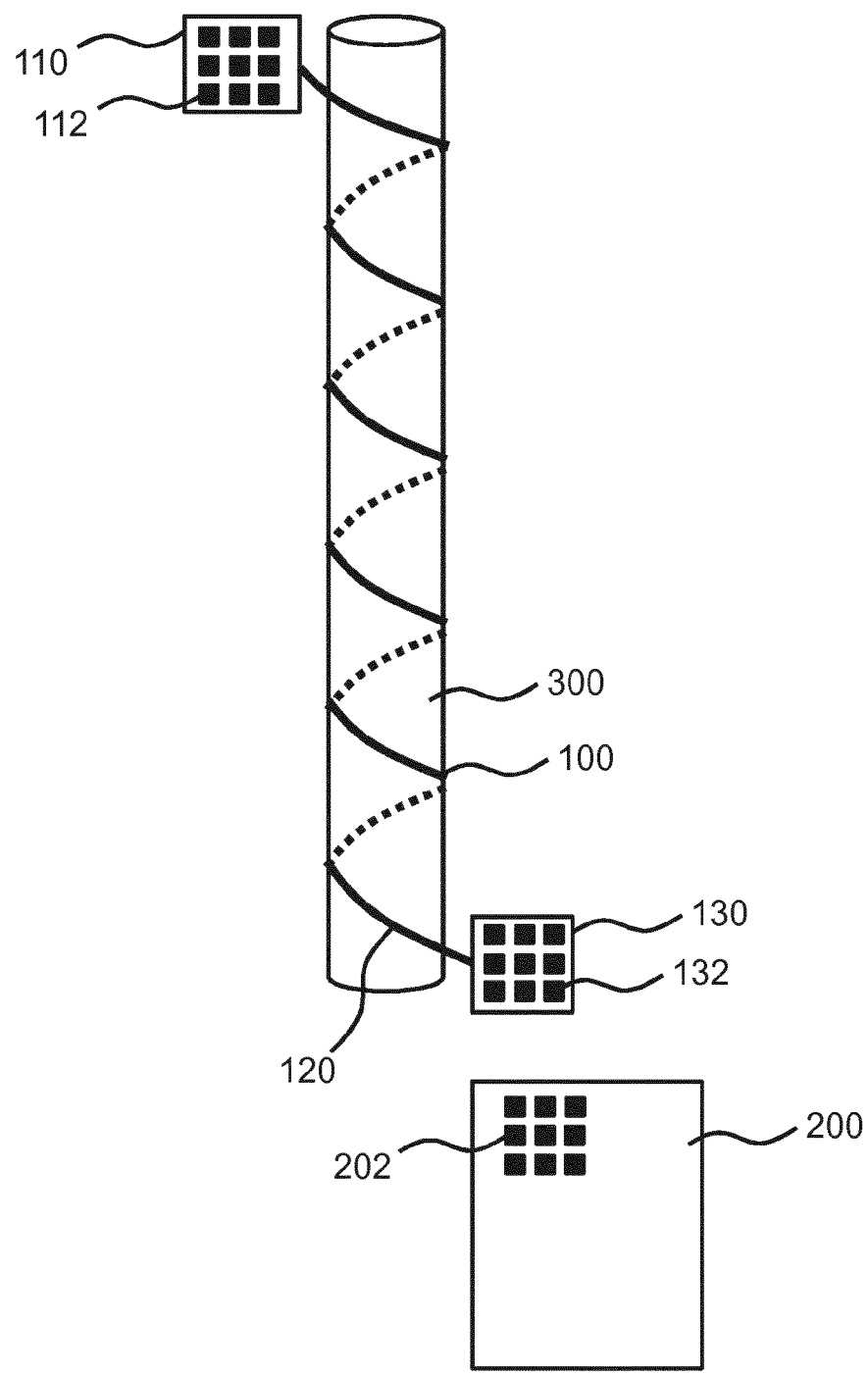
FIG. 5 schematically depicts a neurostimulation system according to an embodiment of the present invention.

FIG. 5 schematically depicts a neurostimulation system 1 including the flexible conductive track arrangement 100 according to an embodiment of the present invention and a neurostimulation device 200. The strip 120 of the flexible conductive track arrangement 100 is typically wound around a carrier 300, e.g. a lead body, such that the proximal portion 130 including contacts 132 may be brought into contact with further contacts 202 of the neurostimulation device 200, whilst the distal portion 110 including electrodes 112 may be brought into contact with a tissue area to be stimulated, such as a part of a cochlea or part of the brain of a subject, which may be a human or animal subject. To this end, it is a design objective to minimize the diameter of the carrier 300, in order to reduce physical discomfort to the subject or indeed facilitate the implantation of the carrier 300 including the aforementioned part of the flexible conductive track arrangement 100 altogether. The achievable diameter of the carrier 300 is typically determined by how tight the strip 120 of the flexible track arrangement 100 can be wound around such a carrier 300; i.e. by the diameter of a single turn or pitch of the strip 120.

Due to the use of ALD dielectric layers in the flexible conductive track arrangement 100, a flexible conductive track arrangement 100 can be provided that can be wound more tightly around such a carrier 300 than prior art arrangements. in particular, because the use of ALD dielectric layers facilitates a ceramic dielectric layer stack embedding the metal structures having a reduced thickness, e.g. a maximum thickness of less than 100 nm as previously explained, lest stress is generated within the flexible conductive track arrangement 100 upon bending the arrangement, which facilitates small diameter windings, and a small diameter carrier 300 as a result. At the same time, the barrier properties of the ceramic layers are not compromised due to increased pinholes or defects in such layer. The substantially flat major surface of the polymer coating, i.e. the substantially flat or planar major surface of the first biocompatible polymer layer 18, further reduces the stress in the flexible conductive track arrangement 100 upon bending the arrangement, such that this facilitates a further reduction in the diameter of the carrier 300.

The carrier 300 typically is made of a biocompatible material, such as a biocompatible polymer or a biocompatible metal. Such materials are well-known per se and it is simply noted for the sake of brevity that any suitable biocompatible material may be used for the carrier 300.

Any suitable neurostimulation device 200 may be used, such as a device to stimulate a cochlear implant device or a brain implant device as previously explained. Also other nerve systems may be stimulated with the device of the invention.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A flexible conductive track arrangement, comprising:
    a distal portion comprising a plurality of electrodes;
    a proximal portion comprising a plurality of contacts;
    a strip between the distal portion and the proximal portion, the strip comprising a plurality of conductive tracks, each track connecting an electrode to a contact, wherein the conductive tracks are embedded in an dielectric layer, said dielectric layer being embedded in a biocompatible polymer layer, wherein the biocompatible polymer layer has at least one outer polymer surface that is substantially flat and wherein the dielectric layer has a thickness of less than 500 nm; and
    a central rod, wherein the flexible conductive track is wound around the central rod in a spiralling fashion with the substantially flat surface facing the central rod.

2. The flexible conductive track arrangement of claim 1, wherein the dielectric layer has a thickness of less than 300 nm.

3. The flexible conductive track arrangement of claim 1, wherein the dielectric layer comprises at least one of silicon oxide, silicon nitride, aluminum oxide, and other inorganic oxide.

4. A neurostimulation device, comprising:
    a flexible conductive track arrangement comprising:
        a distal portion including a plurality of electrodes;
        a proximal portion comprising a plurality of contacts;
        a strip between the distal portion and the proximal portion, the strip comprising a plurality of conductive tracks, each track connecting an electrode to a contact, wherein the conductive tracks are embedded in an dielectric layer, the dielectric layer being embedded in a biocompatible polymer layer, wherein the biocompatible polymer layer has at least one outer polymer surface that is substantially flat and wherein the dielectric layer has a thickness of less than 500 nm; and
        a central rod, wherein the flexible conductive track is wound around the central rod in a spiralling fashion with the substantially flat surface facing the central rod; and
    a neurostimulation detection having a plurality of further contacts for contacting respective contacts of the proximal portion of the flexible conductive track arrangement.

5. A hearing aid device comprising the neurostimulation device of claim 4.

* * * * *